United States Patent [19]

Wierenga

[11] 4,086,254
[45] Apr. 25, 1978

[54] PHOTOCLEAVABLE STEROIDS

[75] Inventor: Wendell Wierenga, Kalamazoo, Mich.

[73] Assignee: The Upjohn Company, Kalamazoo, Mich.

[21] Appl. No.: 787,167

[22] Filed: Apr. 13, 1977

[51] Int. Cl.² ............................................. C07J 5/00
[52] U.S. Cl. ............................ 260/397.45; 260/239.55 D
[58] Field of Search ............................................. 260/397.45

[56] References Cited
U.S. PATENT DOCUMENTS

| 2,183,589 | 12/1939 | Reichstein et al. | 260/397.45 |
| 2,862,938 | 12/1958 | Rebenstorf | 260/397.45 |

Primary Examiner—Elbert L. Roberts
Attorney, Agent, or Firm—John J. Killinger; Roman Saliwanchik

[57] ABSTRACT

This invention relates to novel compounds of the formula:

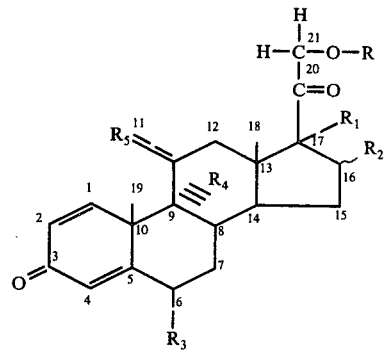

R is

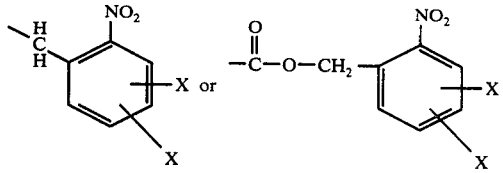

wherein X is H, methoxy, bromine or chloro; $R_1$ is hydrogen or hydroxy, acyloxy wherein acyl is 2 to 8 carbon atoms, $R_2$ is hydrogen, hydroxy, methyl, fluoro or chloro; and $R_1$ and $R_2$ taken together can be

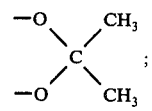

$R_3$ is hydrogen, methyl, chloro, or fluoro; $R_4$ is hydrogen, chloro or fluoro; $R_5$ is oxygen, $\beta$-hydroxy or $\beta$-chloro, with the proviso that when $R_5$ is $\beta$-chloro then $R_4$ must be chloro.

The compounds have a photocleavable group (R) which is removable by irradiation. The compounds have reduced activity in the uncleaved state and provide a therapeutically active compound upon irradiation at the site of irradiation.

7 Claims, No Drawings

PHOTOCLEAVABLE STEROIDS

BRIEF DESCRIPTION OF THE INVENTION

This invention relates to novel compounds which when administered systemically do not exhibit appreciable thereapeutic activity or side effects. The drugs are distributed throughout the body and at the locus of desired therapeutic effect, primarily the skin, the therapeutic form of the drug is released by irradiation.

DETAILED DESCRIPTION OF THE INVENTION

This invention relates to chemical compounds which are succeptable to cleavage by irradiation, one portion of the cleaved compound being a therapeutically active anti-inflammatory steroid.

Previous therapy involving the use of anti-inflammatory compounds required the systemic administration of the compound to allow it to reach the site of the desired therapeutic effect. In treating skin diseases, this mode of administration had the undesirable consequence of exposing the whole body to the effects of the steroid. Alternatively to avoid the exposure of the body to the steroid, topical application was utilized having the disadvantage of poor absorption and low therapeutic levels of drug.

The present invention allows the systemic administration of a compound with diminished or no therapeutic activity which when exposed to irradiation at the desired site of action releases the therapeutically useful form of the drug.

This is accomplished by administering a compound of the formula I:

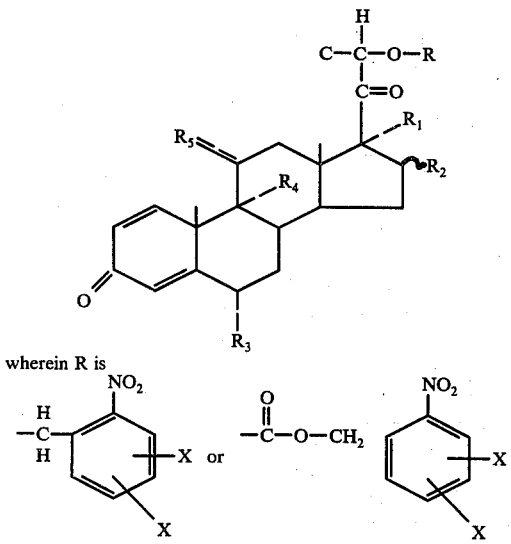

wherein R is

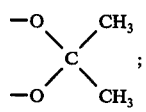

X is H, methoxy, bromine or chloro; $R_1$ is hydrogen or hydroxy, acyloxy wherein acyl is from 2 to 8 carbon atoms, inclusive; $R_2$ is hydrogen, hydroxy, methyl, fluoro or chloro; and $R_1$ and $R_2$ taken together can be $$-O\diagdown C \diagup CH_3 \atop -O \diagup \diagdown CH_3$$

$R_3$ is hydrogen, methyl, chloro, or fluoro; $R_4$ is hydrogen, chloro or fluoro; $R_5$ is oxygen, β-hydroxy or β-chloro, with the proviso that when $R_5$ is β-chloro then $R_4$ must be chloro, and irradiating that part of the body where the desired therapeutic effect is required.

The more preferred compounds are those of the formula II:

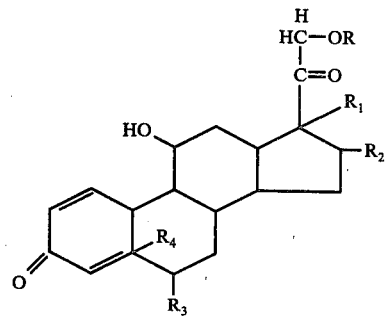

wherein R is selected from the group consisting of

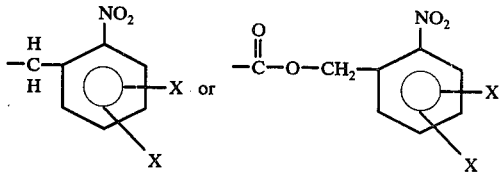

X is selected from H, methoxy, bromine or chlorine, $R_1$ is selected from the group consisting of hydrogen or hydroxy; $R_2$ is selected from the group consisting of hydrogen, hydroxy and methyl or $R_2$ together with $R_1$ can be acetonide; $R_3$ is selected from the group consisting of methyl or fluoro; $R_4$ is selected from the group consisting of hydrogen or fluorine.

While the primary benefit of the present invention lies with the systemic route of administration, e.g., orally, rectally, intramuscularly, intravenously, and subcutaneously, topical application is also contemplated.

The quantity of the active compound to be used in the compositions of this invention for administration topically, parenterally or systemically ranges from about 0.1% to about 15% weight/weight topically; from about 0.1% to about 10% w/v parenterally; and for oral dosage forms the % amount of active ingredient is determined by the physical characteristics of the carrier with regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water, water-oil emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more imcompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule of appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compounds of the formula I the dosage range is 1-20 times the dosage of the compounds of the formula I wherein R is hydrogen.

The active compounds of the present invention are prepared by reacting compounds of the formula I wherein R is hydrogen with a compound of the formula:

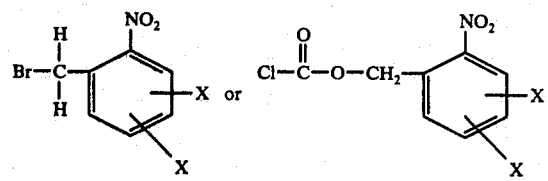

under an inert atmosphere such as nitrogen in $N_2$ and in an inert solvent, e.g., dimethylformamide, tetrahydrofuran, dimethylsulfoxide, hexamethylphosphoramide, benzene, toluene, xylene, etc., in the presence of a halogen scavenger and base, e.g., silver oxide.

The final compound can be separated and purified by conventional techniques, e.g., chromatography.

The compounds should be protected from light.

The therapeutically active form of the compound as released at the desired site of action by irradiation with ultraviolet light, i.e., light having a wave length of from about 2500 to 4000 angstroms, a preferred range is from about 3100 to 3700 angstroms and especially preferred is a range of from 3500 to 3600 angstroms. The intensity of the irradiation can be from 1 to 40 joules/cm² of skin area with an intensity of 3-20 joules/cm² of skin preferred in a single exposure or repeated several times daily.

The new anti-inflammatory steroids can be used to treat all the diseases that steroids are known to be useful to treat, particularly those disease conditions which are of a dermatological nature, including, but not limited to, proliferative skin diseases.

The expression "proliferative skin diseases" means benign and proliferative skin diseases which are characterized by epidermal cell proliferation, or division, and may also be associated with incomplete tissue differentiation. Psoriasis is the most serious of the skin diseases with which this invention is concerned. Such diseases include psoriasis, atopic dermatitis, non-specific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis in domesticated animals.

The following examples are illustrative of the process and products of the present invention but are not to be construed as limiting.

EXAMPLE 1

11β,17-Dihydroxy-6α-methyl-21-[(o-nitrobenzyl)oxy]-pregna-1,4-diene-3,20-dione

6α-Methylprednisolone (1.86 g., 5 mmole) is dissolved in 20 ml. of dry dimethylformamide (distilled from calcium hydride). This is placed under nitrogen and silver oxide (1.3 g., 5.5 mmole), o-nitrobenzyl bromide (2.65 g., 12 mmole) and N,N-diisopropylethyl amine (2.5 ml.) are added with stirring. The mixture is heated to 50° C. for one hour and more silver oxide (1.3 g.) and o-nitrobenzyl bromide (2.65 g.) are added and the reaction continued for 5.5 hours. The reaction mixture is poured into 200 ml. of ethyl acetate and diluted with 100 ml. of brine. After shaking the organic layer is separated, dried over sodium sulfate and concentrated in vacuo. The residue is chromatographed on 400 g. of silica gel using 40% ethyl acetate-hexane (600 ml.) followed by 60% ethyl acetate-hexane. Fractions with Rf value 0.5–0.65 as determined by thin layer chromatography (85% ethyl acetate-hexane) are recovered (1.2 g.) and rechromatographed using 40% ethyl acetate-hexane on 150 g. silica gel column. The fractions with Rf = 0.60 are recovered to give 450 mg. of 11$\beta$,17-dihydroxy-6$\alpha$-methyl-21-[(o-nitrobenzyl)oxy]-pregna-1,4-diene-3,20-dione as a light yellow solid and having a melting point of 116°–119° C. (unrecrystallized).

Analysis: Calc'd. for $C_{29}H_{35}NO_7$: C, 68.35; H; 6.92; N; 2.75; Found: C, 69.30; H; 7.33; N; 2.81.

EXAMPLE 2

11$\beta$,17-Dihydroxy-9$\alpha$-fluoro-16$\alpha$-methyl-21-[(o-nitrobenzyl)oxy]pregna-1,4-diene-3,20-dione Following the procedure of Example 1 but substituting 9$\alpha$-fluoro-11$\beta$,17$\alpha$,21-trihydroxy-16$\alpha$-methyl-1,4-pregnadiene-3,20-dione for the 6$\alpha$-methylprednisolone there is obtained 11$\beta$,17$\alpha$-dihydroxy-9$\alpha$-fluoro-16$\alpha$-methyl-21-[(o-nitrobenzyl)oxy]pregna-1,4-diene-3,20-dione as a light yellow solid of m.p. 102°–106° C. (unrecrystallized).

Analysis: Calc'd. for $C_{29}H_{34}FNO_7$: C, 66.02; H; 6.50; N; 2.65; Found: C, 64.58; H; 6.55; N; 2.81.

EXAMPLE 3

11$\beta$,17-dihydroxy-6$\alpha$-methyl-21-[(3,4-dimethoxy-6-nitrobenzyl)oxy]-pregna-1,4-diene-3,20-dione Following the procedure of Example 1 but substituting 3,4-dimethoxy-6-nitrobenzyl bromide for the o-nitrobenzyl bromide and increasing the reaction period to 40 hours there is obtained 11$\beta$,17-dihydroxy-6$\alpha$-methyl-21-[(3,4-dimethoxy-6-nitrobenzyl)oxy]pregna-1,4-diene-3,20-dione as a yellow solid.

In the manner given in Examples 1–3 other steroids of the formula I can be prepared starting with compounds of formula I wherein R is hydrogen. Representative compounds, there obtained, include:

11$\beta$,17$\alpha$-dihydroxy-6$\alpha$-methyl-21-[(2-nitro-4-chlorobenzyl)oxy]-pregna-1,4-diene-3,20-dione, 11$\beta$,17$\alpha$-dihydroxy-6$\alpha$-methyl-21-[(2-nitro-3-bromobenzyl)oxy]-pregna-1,4-diene-3,20-dione, 11$\beta$,17$\alpha$-dihydroxy-6$\alpha$-methyl-21-[(4,5-dichloro-2-nitrobenzyl)oxy]-pregna-1,4-diene-3,20-dione, 11$\beta$,17$\alpha$-dihydroxy-6$\alpha$-methyl-21-[(4-methoxy-2-nitrobenzyl)oxy]-pregna-1,4-diene-3,20-dione, 11$\beta$,17$\alpha$-dihydroxy-6$\alpha$-methyl-9$\alpha$-fluoro-21-[(o-nitrobenzyl)oxy]-pregna-1,4-diene-3,20-dione, 11$\beta$,17$\alpha$-dihydroxy-6$\alpha$,9$\alpha$-difluoro-21-[(2-nitro-4,5-dimethoxybenzyl)oxy]-pregna-1,4-diene-3,20-dione, 17$\alpha$-hydroxy-9$\alpha$,11$\beta$-dichloro-6$\alpha$-methyl-21-[(o-nitrobenzyl)oxy]-pregna-1,4-diene-3,20-dione, 17$\alpha$-hydroxy-11-keto-6$\alpha$-methyl-16-fluoro-21-[(o-nitrobenzyl)oxy]-pregna-1,4-diene-3,20-dione, 11$\beta$,16$\alpha$,17$\alpha$-trihydroxy-6$\alpha$-chloro-4$\alpha$-fluoro-16,17-acetonide-21-[(4-chloro-2-nitrobenzyl)oxy]-pregna-1,4-diene-3,20-dione, 11$\beta$-hydroxy-9$\alpha$-chloro-16$\alpha$-methyl-21-[(o-nitrobenzyl)oxy]-pregna-4-ene-3,20-dione, 6$\alpha$-fluoro-9$\alpha$,11$\beta$-dichloro-16$\alpha$,17$\alpha$-dihydroxy-16,17-acetonide-21-[(o-nitrobenzyl)oxy]-pregna-4-ene-3,20-dione, 6$\alpha$,9-difluoro-11$\beta$,17-dihydroxy-16$\beta$-methyl-21-[(o-nitrobenzyl)oxy]-pregna-1,4-diene-3,20-dione, 6$\alpha$,9-difluoro-11$\beta$,17-dihydroxy-16$\beta$-methyl-17-acetoxy-21-[(o-nitrobenzyl)oxy]-pregna-1,4-diene-3,20-dione, 11$\beta$,17-dihydroxy-9$\alpha$-fluoro-16$\alpha$-methyl-21-[(2-nitro-4-methoxybenzyl)oxy]-pregna-1,4-diene-3,20-dione, 11$\beta$,16,17-trihydroxy-6$\alpha$-methyl-9$\alpha$-fluoro-21-[(2-nitro-4-chlorobenzyl)oxy]-pregna-1,4-diene-3,20-dione, 11$\beta$,17-dihydroxy-6$\alpha$,16$\alpha$-dimethyl-21-[(2-nitro-4-chloro-5-methoxybenzyl)oxy]-pregna-1,4-diene-3,20-dione, 11$\beta$,17-dihydroxy-6$\alpha$,16$\alpha$-dimethyl-9$\alpha$-fluoro-21-[(o-nitrobenzyl)oxy]-pregna-1,4-diene-3,20-dione.

EXAMPLE 4

11$\beta$,17$\alpha$-Dihydroxy-6$\alpha$-methyl-21-[(o-nitrobenzyl)oxycarbonyl]oxy-pregna-1,4-diene-3,20-dione To 6$\alpha$-methylprednisolone (5.58 g., 15 mmole) in 75 ml. of dry pyridine under nitrogen at room temperature, with stirring, is added o-nitrobenzyloxycarboxyl chloride (4.30 g., 20 mmole) dropwise over 5 minutes. The reaction is allowed to stir for 16 hours and the 200 ml. of ethyl acetate and 100 ml. of water are added. The organic phase is separated and washed once with 100 ml. of 0.1 N hydrochloric acid, followed by brine, dried over sodium sulfate and concentrated in vacuo. The residue is chromatographed on 200 g. silica gel column using 70% ethyl acetate-hexane and recrystallized from ethyl acetate to give 11$\beta$,17$\alpha$-dihydroxy-6$\alpha$-methyl-21-[(o-nitrobenzyl)oxycarbonyl]oxy-pregna-1,4-diene-3,20-dione of m.p. 198°–199° C.

Analysis: Calc'd. for $C_{30}H_{35}NO_9$: C, 65.08; H; 6.37; N; 2.53; Found: C, 64.95; H; 6.44; N; 2.41.

EXAMPLE 5

11$\beta$,17-Dihydroxy-9$\alpha$-fluoro-16$\alpha$-methyl-21-[(o-nitrobenzyl)oxycarbonyl]oxy-pregna-1,4-diene-3,20-dione Following the procedure of Example 4 but substituting 11$\beta$,17,21-trihydroxy-9$\alpha$-fluoro-16$\alpha$-methylpregna-1,4-diene-3,20-dione for the 6$\alpha$-methylprednisolone there is obtained 11$\beta$,17-dihydroxy-9$\alpha$-fluoro-16$\alpha$-methyl-21-[(o-nitrobenzyl)oxycarbonyl]oxy-pregna-1,4-diene-3,20-dione of m.p. 203°–204° C. (recrystallized twice from acetone).

Analysis: Calc'd. for $C_{30}H_{34}FNO_9$: C, 63.04; H; 6.00; N; 2.45; Found: C, 62.19; H; 6.03; N; 2.52.

EXAMPLE 6

9$\alpha$-Fluoro-21-[(o-nitrobenzyl)oxycarbonyl]oxy-11$\beta$,16,17-trihydroxypregna-1,4-diene-3,20-dione Following the procedure of Example 4 but substituting 11$\beta$,16,17$\alpha$,21-tetrahydroxy-9$\alpha$-fluoropregna-1,4-diene-3,20-dione for 6$\alpha$-methylprednisolone there is obtained 9$\alpha$-fluoro-21-[(o-nitrobenzyl)oxycarbonyl]oxy-11$\beta$,16$\alpha$,17$\alpha$-trihydroxypregna-1,4-diene-3,20-dione of m.p. 205°–207° C.

Analysis: Calc'd. for $C_{29}H_{32}FNO_{10}$: C, 60.72; H; 5.62; N; 2.44; Found: C, 59.58; H; 5.48; N; 2.63.

In the manner given in Examples 4–6 other steroids of the formula I can be prepared from compounds of formula II wherein R is hydrogen. Representative compounds, thus obtained, include:

11β,17α-dihydroxy-6α-methyl-21-[(2-nitro-4,5-dimethoxybenzyl)oxycarbonyl]oxy-pregna-1,4-diene-3,20-dione, 11β,17α-dihydroxy-6α,16α-dimethyl-9α-fluoro-21-[(o-nitrobenzyl)oxycarbonyl]oxy-pregna-1,4-diene-3,20-dione, 9α,11β-dichloro-6α-methyl-16α,17α-dihydroxy-21-[(2-nitro-3-bromobenzyl)oxycarbonyl]oxy-pregna-1,4-diene-3,20-dione 16,17-acetonide, 6α,9α-difluoro-11β,16α,17α-trihydroxy-21-[(o-nitrobenzyl)oxycarbonyl]oxy-pregna-1,4-diene-3,20-dione, 6α,9α-difluoro-11β,17α-dihydroxy-16β-methyl-21-[(o-nitrobenzyl)oxycarbonyl]oxy-pregna-1,4-diene-3,20-dione 17-acetate, 6α,9α-dichloro-11-keto-21-[(3,4-dichloro-2-nitrobenzyl)oxycarbonyl]oxy-pregna-1,4-diene-3,20-dione, 11β,17-dihydroxy-6α-methyl-21-[(o-nitrobenzyl)oxycarbonyl]oxy-pregna-4-ene-3,20-dione, 6α-methyl-9α-chloro-11β,16α,17α-trihydroxy-16,17-acetonide-21-[(3-bromo-4-chloro-2-nitrobenzyl)oxycarbonyl]oxy-pregna-1,4-diene-3,20-dione, 9α-fluoro-11β-hydroxy-21-[(o-nitrobenzyl)oxycarbonyl]oxy-pregna-1,4-diene-3,20-dione, 6α,9-difluoro-11β,17-dihydroxy-16β-methyl-21-[(o-nitrobenzyl)oxycarbonyl]oxy-pregna-4-ene-3,20-dione, 6α,9α-difluoro-16-chloro-11β,17α-dihydroxy-21-[(2-nitro-3,6-dibromobenzyl)oxycarbonyl]oxy-pregna-1,4-diene-3,20-dione, 6α,16α-dimethyl-9α,11β-dichloro-17α-hydroxy-21-[(o-nitrobenzyl)oxycarbonyl]oxy-pregna-1,4-diene-3,20-dione 17-acetate, 6α,9α,16-trifluoro-21-[(o-nitrobenzyl)oxycarbonyl]oxy-pregna-1,4-diene-3,11,20-trione, 9α-fluoro-11β,16α,17α-trihydroxy-21-[(o-nitrobenzyl)oxycarbonyl]oxy-pregna-1,4-diene-3,20-dione 16,17-acetonide.

EXAMPLE 7

Capsules

One thousand two-piece hard gelatin capsules for oral use, each containing 1.0 mg. of 11β,17-dihydroxy-6α-methyl-21-[(o-nitrobenzyl)oxy]-pregna-1,4-diene-3,20-dione are prepared from the following types and amounts of materials:

| | | |
|---|---|---|
| 11β,17-dihydroxy-6α-methyl-21-[(o-nitrobenzyl)oxy]-pregna-1,4-diene-3,20-dione | 1.0 | gm. |
| Talc | 150 | gm. |
| Magnesium stearate | 85 | gm. |
| Corn starch | 300 | gm. |
| Lactose | 100 | gm. |

The materials are thoroughly mixed and then encapsulated in the usual manner.

The foregoing capsules are useful for the systemic treatment of psoriasis in adult humans by the oral administration of 1 capsule every 4 hours followed by irradiation of the psoriatic lesions with 5 joules/cm².

Using the procedure above, capsules are similarly prepared containing in 0.5, 2.0, and 5.0 mg. amounts by substituting 0.5, 2.0, and 5.0 gm. of 11β,17-dihydroxy-6α-methyl-21-[(o-nitrobenzyl)oxy]-pregna-1,4-diene-3,20-dione for the 1.0 gm. used above.

EXAMPLE 8

Tablets

Ten thousand tablets for oral use are prepared from the following types and amounts of material:

| | | |
|---|---|---|
| 11β,17-dihydroxy-9α-fluoro-16α-methyl-21-[(o-nitrobenzyl)oxy]-pregna-1,4-diene-3,20-dione | 25 | gm. |
| Lactose | 900 | gm. |
| Corn starch | 125 | gm. |
| Magnesium stearate | 10 | gm. |
| Light liquid petrolatum | 25 | gm. |

The ingredients are thoroughly mixed and slugged. The slugs are broken down by forcing through a number sixteen screen. The resulting granules are then compressed into tablets, each tablet containing 2.5 mg. of 11β,17-dihydroxy-9α-fluoro-16α-methyl-21-[(o-nitrobenzyl)oxy]-pregna-1,4-diene-3,20-dione.

The foregoing tablets are useful for systemic treatment of psoriasis in adult humans by oral administration of 1 tablet every 4 hours followed by irradiation of the psoriatic lesions with 1 joule/cm².

EXAMPLE 9

Parenteral solution

A sterile aqueous solution for intramuscular use, containing in 1 cc. 5 mg. of 11β,17-dihydroxy-6α-methyl-21-[(3,4-dimethoxy-6-nitrobenzyl)oxy]-pregna-1,4-diene-3,20-dione is prepared from the following types and amounts of materials:

| | | |
|---|---|---|
| 11β,17-dihydroxy-6α-methyl-21-[(3,4-dimethoxy-6-nitrobenzyl)oxy]-pregna-1,4-diene-3,20-dione | 5 | gm. |
| Lidocaine hydrochloride | 4 | gm. |
| Methylparaben | 2.5 | gm. |
| Propylparaben | 0.17 | gm. |
| Water for injection q.s. | 1000 | cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day followed by irradiation of the psoriatic lesions with 20 joules/cm².

EXAMPLE 10

Parenteral solution

A sterile aqueous solution for intradermal use, containing in 1 cc. 5 mg. of 11β,17-dihydroxy-6α-methyl-21-[(o-nitrobenzyl)oxy]-pregna-1,4-diene-3,20-dione is prepared from the following types and amounts of ingredients:

| | | |
|---|---|---|
| 11β,17-dihydroxy-6α-methyl-21-[(o-nitrobenzyl)oxy]-pregna-1,4-diene-3,20-dione | 5 | gm. |
| Sodium chloride 10% solution q.s. | | |
| Water for injection q.s. | 1000 | cc. |

The 11β,17-dihydroxy-6α-methyl-21-[(o-nitrobenzyl)oxy]-pregna-1,4-diene-3,20-dione is added to the water and sufficient sodium chloride added to form an isotonic solution and the solution sterilized by filtration.

The sterile solution is administered intradermally by high pressure injection for treatment of psoriasis on the area irradiated with 40 joules/cm$^2$.

EXAMPLE 11

Cream

One thousand grams of a topical cream are prepared from the following types and amounts of ingredients:

| | | |
|---|---|---|
| 11β,17-dihydroxy-6α-methyl-21-[(o-nitrobenzyl)oxy]-pregna-1,4-diene-3,20-dione | 90 | gm. |
| Tegacid Regular* | 150 | gm. |
| Spermaceti | 100 | gm. |
| Propylene glycol | 50 | gm. |
| Polysorbate 80 | 5 | gm. |
| Methylparaben | 1 | gm. |
| Deionized water q.s. | 1000 | gm. |

*Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm. of water and the propylene glycol, polysorbate 80, and 11β,17-dihydroxy-6α-methyl-21-[(o-nitrobenzyl)oxy]-pregna-1,4-diene-3,20-dione are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occlusive bandage for six hours followed by removal of the bandage and cream and irradiation of the area with 10 joules/cm$^2$.

EXAMPLE 12

Following the procedure of the preceding Examples 9 to 13 inclusive, substituting an equimolar amount of
11β,17α-dihydroxy-6α-methyl-21-[(o-nitrobenzyl)oxy]-pregna-1,4-diene-3,20-dione,
11β,17α-dihydroxy-9α-fluoro-16α-methyl-21-[(o-nitrobenzyl)oxy]-pregna-1,4-diene-3,20-dione,
11β,17α-dihydroxy-6α-methyl-21-[(3,4-dimethoxy-6-nitrobenzyl)oxy]-pregna-1,4-diene-3,20-dione,
11β,17α-dihydroxy-6α-methyl-21-o-[(o-nitrobenzyl)oxycarbonyl]-pregna-1,4-diene-3,20-dione,
11β,17α-dihydroxy-9α-fluoro-16α-methyl-21-o-[(o-nitrobenzyl)oxycarbonyl]-pregna-1,4-diene-3,20-dione,
9α-fluoro-21-o-[(o-nitrobenzyl)oxycarbonyl]-11β,16α,17α-trihydroxypregna-1,4-diene-3,20-dione,
6α,9-difluoro-11β,17-dihydroxy-16β-methyl-21-[(o-nitrobenzyl)oxy]-pregna-1,4-diene-3,20-dione,
6α,9-difluoro-11β,17-dihydroxy-16β-methyl-21-o-[(o-nitrobenzyl)oxycarbonyl]oxy-pregna-1,4-diene-3,20-dione for the 11β,17-dihydroxy-6α-methyl-21-[(o-nitrobenzyl)oxy]-pregna-1,4-diene-3,20-dione composition are similarly prepared and used.

EXAMPLE 13

Following the procedure of the preceding Examples 9 through 14, inclusive, the compositions are used in the treatment of atopic dermatitis, non-specific dermatitis, primary irritant dermatitis, allergic contact dermatitis, lamellar ichthyosis, epidermolytic hyperkeratosis, premalignant sun induced keratosis, non-malignant keratosis, or seborrheic dermatitis in humans and atopic dermatitis in animals.

I claim:

1. A compound of the formula:

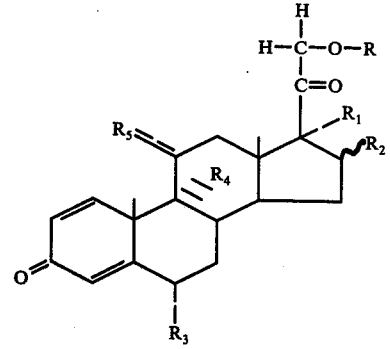

wherein R is

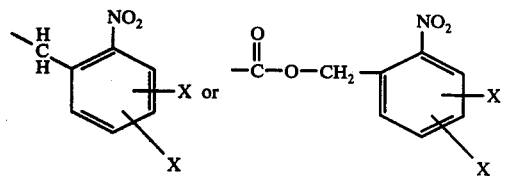

X is H, methoxy, bromine, or chloro; $R_1$ is hydrogen or hydroxy, acyloxy wherein acyl is from 2–8 carbon atoms, inclusive; $R_2$ is hydrogen, hydroxy, methyl, fluoro, or chloro; and $R_1$ and $R_2$ taken together can be

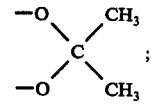

$R_3$ is hydrogen, methyl, chloro, or fluoro; $R_4$ is hydrogen, chloro or fluoro; $R_5$ is oxygen, β-hydroxy or β-chloro with the proviso that when $R_5$ is β-chloro $R_4$ is chloro.

2. A compound according to claim 1 which is 11,17-dihydroxy-6-methyl-21-[(o-nitrobenzyl)oxy]-pregna-1,4-diene-3,20-dione.

3. A compound according to claim 1 which is 11β,17α-dihydroxy-9α-fluoro-16α-methyl-21-[(o-nitrobenzyl)oxy]-pregna-1,4-diene-3,20-dione.

4. A compound according to claim 1 which is 11β,17α-dihydroxy-6α-methyl-21-[(3,4-dimethoxy-6-nitrobenzyl)oxy]-pregna-1,4-diene-3,20-dione.

5. A compound according to claim 1 which is 11β,17α-dihydroxy-6α-methyl-21-o-[(o-nitrobenzyl)oxycarbonyl]-pregna-1,4-diene-3,20-dione.

6. A compound according to claim 1 which is 11β,17α-dihydroxy-9α-fluoro-16α-methyl-21-o-[(o-nitrobenzyl)oxycarbonyl]-pregna-1,4-diene-3,20-dione.

7. A compound according to claim 1 which is 9α-fluoro-21-o-[(o-nitrobenzyl)oxycarbonyl]-11β,16α,17α-trihydroxy-pregna-1,4-diene-3,20-dione.

* * * * *

UNITED STATES PATENT AND TRADEMARK OFFICE
CERTIFICATE OF CORRECTION

PATENT NO. : 4,086,254
DATED : April 25, 1978
INVENTOR(S) : Wendell Wierenga

It is certified that error appears in the above-identified patent and that said Letters Patent are hereby corrected as shown below:

Column 1, line 39,

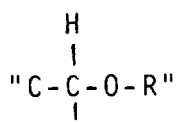

should read

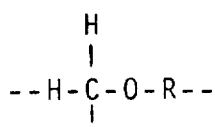

Column 1, line 53, formula should read

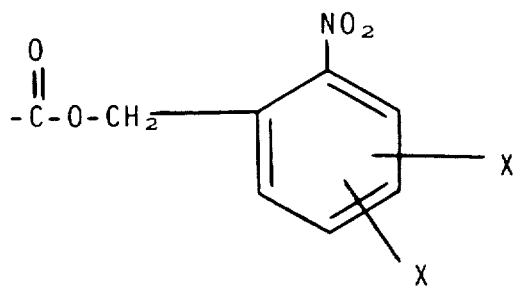

Column 2, lines 8-20, the formula should read

UNITED STATES PATENT AND TRADEMARK OFFICE
CERTIFICATE OF CORRECTION

PATENT NO. : 4,086,254
DATED : April 25, 1978
INVENTOR(S) : Wendell Wierenga

It is certified that error appears in the above-identified patent and that said Letters Patent are hereby corrected as shown below:

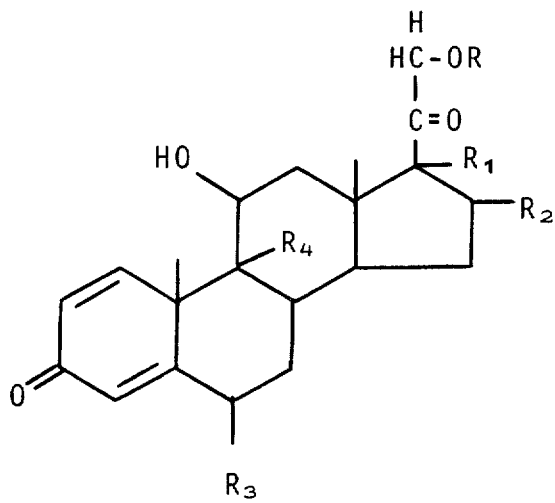

Column 10, lines 49-50, the compound should read --11β,17-dihydroxy-6α-methyl-21-[(o-nitrobenzyl)oxy]-pregna-1,4-diene-3,20-dione.-

Signed and Sealed this

Seventeenth Day of October 1978

[SEAL]

Attest:

RUTH C. MASON
Attesting Officer

DONALD W. BANNER
Commissioner of Patents and Trademarks